United States Patent [19]

Swift

[11] Patent Number: 4,655,765
[45] Date of Patent: Apr. 7, 1987

[54] FITTING WITH PRESTRESSED SEPTUM

[75] Inventor: William G. Swift, Fountain Valley, Calif.

[73] Assignee: Parker Hannifin Corporation, Cleveland, Ohio

[21] Appl. No.: 616,338

[22] Filed: Jun. 1, 1984

[51] Int. Cl.[4] .............................................. A61M 7/00
[52] U.S. Cl. .................................... 604/891; 604/48; 604/140
[58] Field of Search ............... 604/46, 48, 93, 115, 604/116, 124, 51, 52

[56] References Cited

U.S. PATENT DOCUMENTS

| | | | |
|---|---|---|---|
| 3,731,681 | 5/1973 | Blackshear | 604/141 |
| 3,894,538 | 7/1975 | Richter | 128/260 |
| 3,951,147 | 4/1976 | Tucker | 128/260 |
| 3,977,402 | 8/1976 | Pike | 604/51 |
| 4,152,098 | 5/1979 | Moody et al. | 604/153 |
| 4,193,397 | 3/1980 | Tucker et al. | 604/93 |
| 4,221,219 | 9/1980 | Tucker | 128/260 |
| 4,229,220 | 10/1980 | Hirota | 106/47 R |
| 4,360,019 | 11/1982 | Portner et al. | 128/213 R |
| 4,373,527 | 2/1983 | Fischell | 128/260 |
| 4,573,994 | 3/1986 | Fischell et al. | 604/891 |

Primary Examiner—William R. Dixon, Jr.
Assistant Examiner—Margaret B. Medley
Attorney, Agent, or Firm—Frederick L. Tolhurst

[57] ABSTRACT

A medication infusion device (10) wherein a septum fitting (14) includes a housing (50) that cooperates with an annular band (68) and a septum (66) to define a cavity (80). A poppet (84) cooperates with a seating ring (88), annular band (68) and septum (66) to define an antechamber (85), and to form a seal between the septum and a reservior (32). The septum (66) is held in compression between the annular band (68) and a guide (56) to improve resealing of the septum.

9 Claims, 4 Drawing Figures 4,655,765

FITTING WITH PRESTRESSED SEPTUM

BACKGROUND OF THE INVENTION

1. Field of the Invention

The subject invention is directed to mechanisms for accessing the reservoir of implantable medication infusion devices and, more particularly, to resealing septums used in such devices.

2. Description of the Prior Art

Implantable medication infusion devices designed to infuse medication into a patient's body at a controlled dosage and rate have been known in the prior art. These devices have included reservoirs for storing a supply of medication that will permit continued operation of the device for a specified period before the supply must be replenished.

Most prior art infusion devices have included some mechanism to access the reservoir for refilling purposes. Many of those devices have provided a septum for this purpose. The septum was a membrane that could be penetrated by a needle but that would reseal when the needle was withdrawn. Examples of infusion devices incorporating such septums are shown in U.S. Pat. Nos. 3,951,147; 4,221,219; 4,229,220; and 4,360,019 as well as U.S. patent application Ser. No. 439,138 filed Nov. 11, 1982 by Robert E. Fischell One disadvantage of devices employing refill septums as disclosed in the prior art was that, after the septum had been penetrated a number of times, it had a potential for leakage at the point of penetration. Since the infusion devices were intended for human implantation, correction of such a leakage problem would necessitate subjecting the patient to a surgical procedure. Thus, there was a need in the prior art for an improved septum having extended resealing capability.

To reduce the potential for leakage from the infusion device through a septum leak or through various other failure modes, some more recent infusion devices have incorporated reservoirs that are maintained at less than atmospheric pressure. In these devices, leaks would tend to cause body fluids to leak into the reservoir as opposed to permitting medication to escape.

In these below-atmospheric pressure systems, a valve was provided between the septum and the reservoir to isolate the septum from the reservoir and help maintain the lower absolute pressure therein. In one particularly advantageous arrangement, a cavity was provided adjacent the septum with a poppet valve located therein. In the closed position, the poppet valve isolated the septum from the reservoir. The poppet valve could be mechanically opened by a needle inserted through the septum. This was advantageous in that the reservoir could be refilled passively by inserting the needle through the septum to open the poppet valve and then venting the supply of medication to atmospheric pressure. The pressure differential thus established would cause the medication to flow into the reservoir. If the needle was improperly positioned, the poppet valve would not be opened so that there would be no pressure differential to establish flow of the medication out of the vial. This insured that the needle was properly placed through the septum in communication with the reservoir and avoided the possibility that the medication would inadvertently be injected directly into the body. An example of this type of system is shown in U.S. patent application Ser. No. 327,818 filed Dec. 7, 1981 by Robert E. Fischell.

The cavity and poppet valve arrangement for infusion devices having below-atmospheric pressure reservoirs required that the poppet valve engage the septum to form a tight seal therebetween. However, prior art designs for the spetum did not produce a reliable seal between the poppet and the septum. Thus, in addition to a septum having improved resealing capability, there was also a need for an improved seal formed by the poppet.

SUMMARY OF THE INVENTION

In accordance with the subject invention, a septum fitting includes a housing that has an open end and a closed end with a passageway between the interior and exterior of the housing adjacent the closed end. A guide member that has an aperture between its external and internal faces and a central extension from its internal face is secured in the open end of the housing. A septum is located longitudinally adjacent the guide member and contacts the central extension and the internal face of the guide member. An annular band is located adjacent the septum and is oppositely disposed from the guide. The annular band has an aperture that extends between first and second end faces thereof and is aligned with the aperture of the guide member. The annular band also has a ring extension that is located on the first end face. The annular band contacts the septum such that the septum is compressed between the ring extension and the central extension of the guide. Particularly, the longitudinal separation between the ring extension and the central extension is less than the longitudinal separation between the first end face of the annular band and the internal face of the guide member. More particularly, the first end face of the annular band and the internal face of the guide member contact the septum together with the ring extension and the central extension.

Preferably, the septum, annular band and housing cooperate to define a cavity that confines a filter. Also preferably, the fitting includes a seat that is fitted in an annular groove in the second face of the annular band and the cavity contains a poppet that is biased toward the seat to form a seal.

Other details, objects and advantages of the subject invention will become apparent as the following description of a presently preferred embodiment proceeds.

BRIEF DESCRIPTION OF THE DRAWINGS

The accompanying drawings show a presently preferred embodiment of the subject invention wherein.

DESCRIPTION OF THE PREFERRED EMBODIMENT

Figure 1:
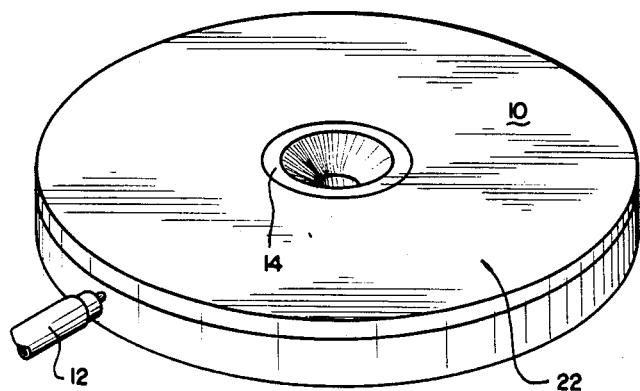
FIG. 1 is a perspective view of an implantable medication infusion device that incorporates a septum fitting in accordance with the subject invention.
Figure 2:
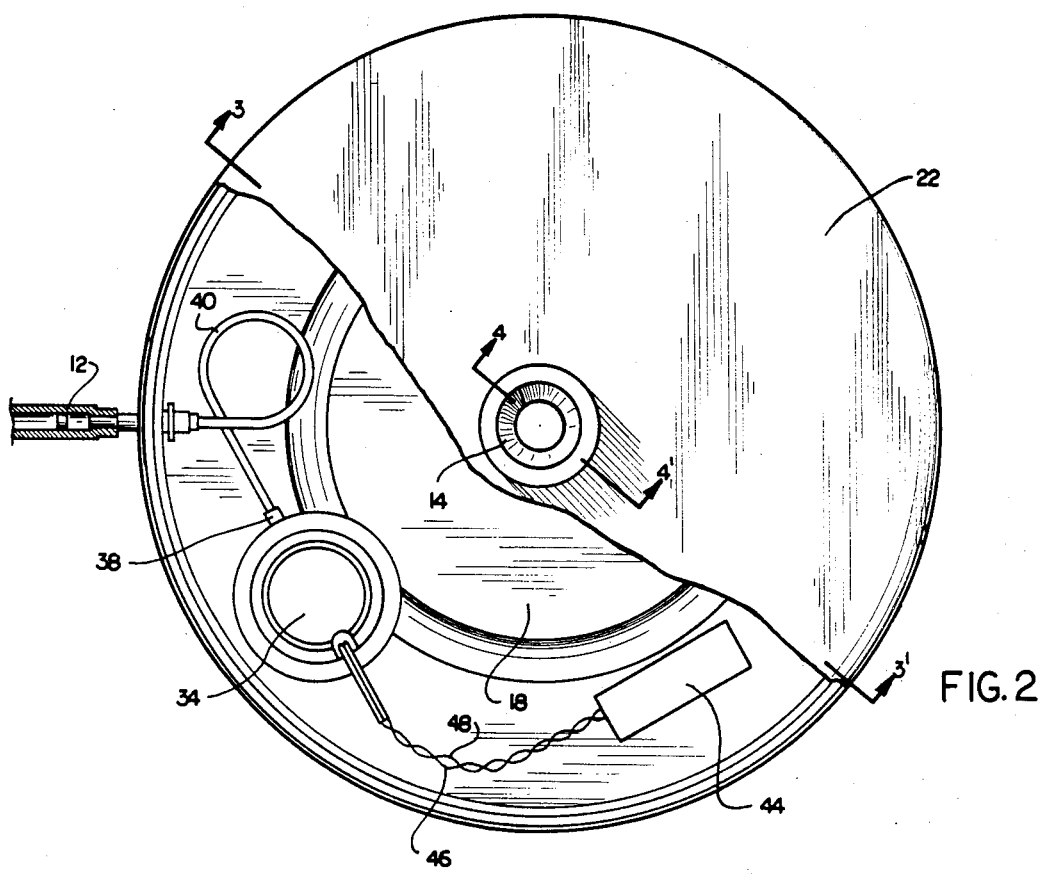
FIG. 2 is a plan view of the device shown in FIG. 1 with portions thereof broken away to better disclose the device.
Figure 3:
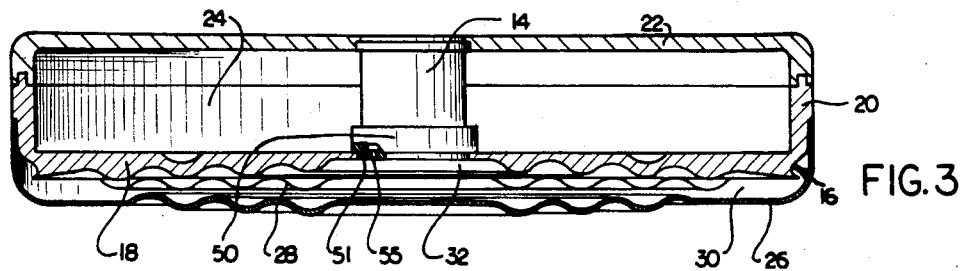
FIG. 3 is a cross-section of the device shown in FIGS. 1 and 2 taken along the lines 3—3' in FIG. 2.

FIGS. 1-3 show an implantable medication infusion device 10 that is connected to a catheter 12 and that incorporates a septum fitting 14 in accordance with the subject invention. Infusion device 10 has a base 16 that includes a manifold 18 with a wall 20 connected to the perimeter thereof. A cover 22 is attached to the distil end of wall 20 and cooperates with base 16 to form a cavity 24. A shell 26 is connected to base 16 and is oppositely disposed from cover 22. A diaphragm 28 is connected to base 16 inside of shell 26. Diaphragm 28 cooperates with shell 26 and base 16 to define a pressurant chamber 30. Diaphragm 28 also cooperates with base 16 to define a reservoir 32.

Pressurant chamber 30 is filled with a gas pressurant such as Freon 113 or an equivalent pressurant that has a vapor pressure at saturation that is slightly less than atmospheric pressure and that will maintain a saturated vapor pressure over the range of normal body temperatures. Thus, the pressurant will maintain a constant pressure in pressurant chamber 30 against diaphragm 28. Accordingly, reservoir 32 is maintained at a fixed pressure that is slightly below atmospheric pressure and that is insensitive to the volume of medication in reservoir 32. Because the fixed pressure in reservoir 32 is slightly below atmospheric pressure, in the event of a leak, medication in reservoir 32 would not be expelled therefrom under pressure.

A pump 34 as shown and described in U.S. application Ser. No. 616,370 entitled "Inverted Pump" by Richard Kenyon and filed concurrently herewith and hereby specifically incorporated by reference, pumps medication that is stored in reservoir 32 to catheter 12. Pump 34 has an input port (not shown) that is connected to reservoir 32 through manifold 18 and an output port 38 that is connected to catheter 12 through a tube 40.

Pump 34 is electrically connected to electrical control circuit 44 through electrical leads 46 and 48. Control circuit 44 can be any suitable control circuit as known in the prior art for activating pump 34 at a controlled rate for a specified time period. Examples of control circuits are shown and described in U.S. Pat. No. 4,373,527; U.S. patent application Ser. No. 439,139 filed Nov. 4, 1982 by Robert E. Fischell; and U.S. patent application Ser. No. 466,494 filed Feb. 15, 1983 by Robert E. Fischell; all of which are hereby specifically incorporated by reference.

Figure 4:
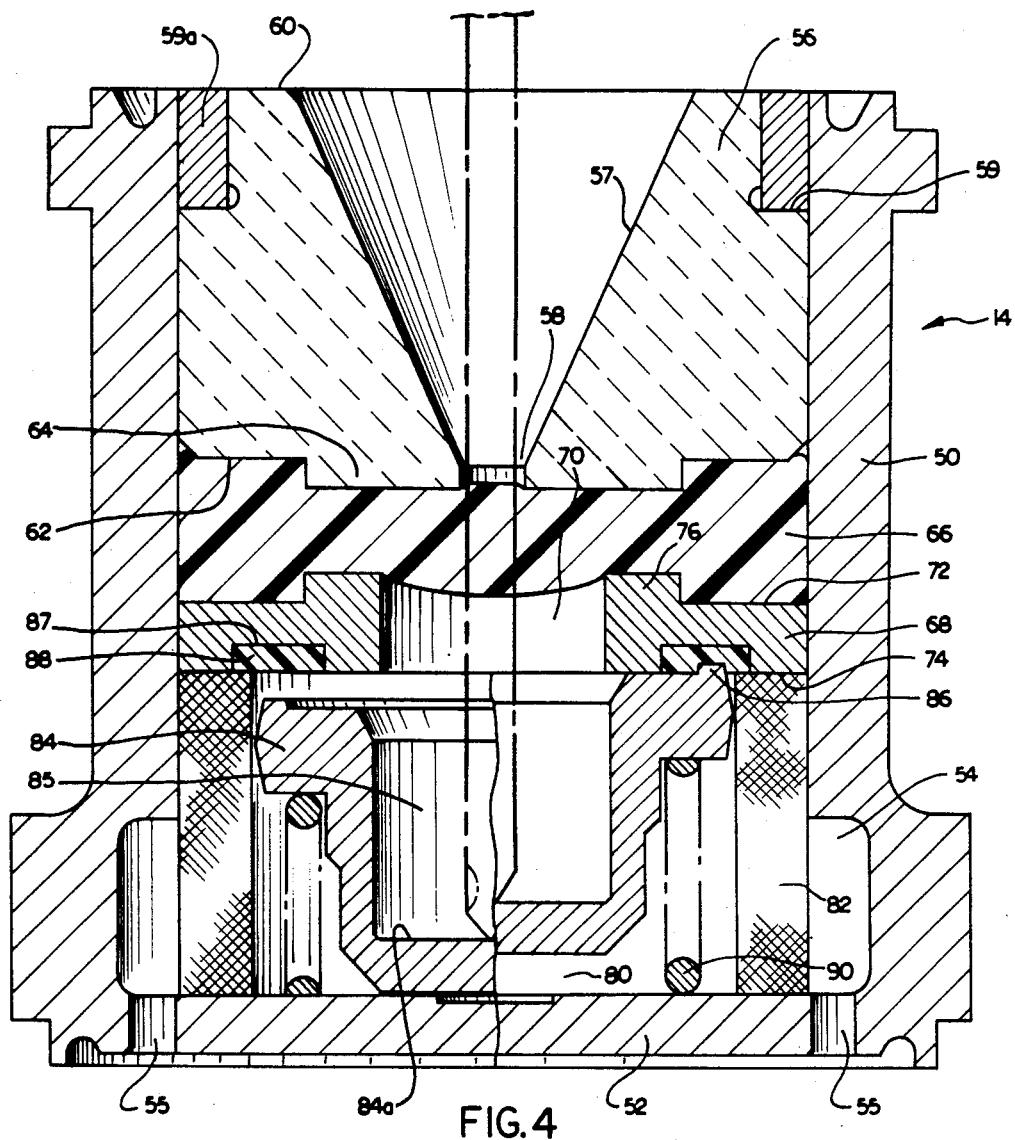
FIG. 4 is an elevation cross-section of the septum fitting incorporated in the device of FIGS. 1-3 taken along the lines 4—4' of FIG. 2 and having a break line to better show the movement of a poppet valve incorporated therein.

Septum fitting 14 is connected to manifold 18 and cover 22 and communicates with reservoir 32 through a bore 51 in manifold 18. As shown in FIG. 4, septum fitting 14 includes a generally cylindrical housing 50 that is fitted in bore 51. Housing 50 has an end wall 52 at one end and is open at the opposite end. Housing 50 has an internal annular groove 54 adjacent end wall 52 and end wall 52 has a plurality of bores 55 that communicate with groove 54 and reservoir 32.

A fill guide 56 that has an outer face 60 and an inner face 62 is located in the open end of housing 50. Fill guide 56 includes an external shoulder 59. A retainer ring 59a is connected adjacent the open end of housing 50 and cooperates with shoulder 59 to retain fill guide 56 in the open end of housing 50. Fill guide 56 also includes a central extension 64 that is located on inner face 62 as well as a conically shaped interior surface 57 and a cylindrical passageway 58. Conical surface 57 is longitudinally aligned in a perpendicular direction between outer face 60 and inner face 62 with the base of conical surface 57 intersecting outer face 60. Cylindrical passageway 58 is located at the apical end of conical surface 57 with one end of passageway 58 intersecting conical surface 57 and the other end of passageway 58 intersecting the end face of extension 64. Thus, conical surface 57 and passageway 58 cooperates to provide a passageway through fill guide 56. Preferably, fill guide 56 is made of ceramic material.

A septum 66 is located inside housing 50 adjacent inner face 62 of fill guide 56. Septum 66 contacts inner face 62 and central extension 64 of fill guide 56. An annular band 68 is located inside housing 50 adjacent the boundary surface of septum 66 that is oppositely disposed from the boundary surface of septum 66 that contacts fill guide 56. Annular band 68 has an aperture 70 that extends between first and second end faces 72 and 74 respectively and is generally aligned with aperture 58 of fill guide 56. Annular band 68 includes a central ring 76 that is located on the first end face 72 and circumscribes aperture 70. Septum 66 also contacts central ring 76 and first end face 72 of annular band 68.

The longitudinal separation between central extension 64 and central ring 76 is less than the longitudinal separation of the inner face 62 of fill guide 56 and the first face 72 of annular band 68. The design of septum fitting 14 is such that the longitudinal separation between central extension 64 and central ring 76 places septum 66 in compression therebetween and causes the septum to partially flow in a radial direction from between central extension 64 and central ring 76 and establish radially directed internal forces within septum 66.

Annular band 68 cooperates with housing 50 and septum 66 to define a cavity 80 that contains an annular filter 82. As hereafter explained, annular filter 82 filters medication as it is delivered to reservoir 32. In addition, annular filter 82 longitudinally locates annular band 68 with respect to end wall 52. More specifically, ring 59a cooperates with external shoulder 59 of fill guide 56, end wall 52 of housing 50, and filter 82 to locate the longitudinal position of fill guide 56 with respect to annular band 68 such that septum 66 is maintained in compression between central extension 64 and central ring 76.

A poppet 84 cooperates with annular ring 68 and septum 66 to define an antechamber 85. Poppet 84 includes a lip portion 86 and is concentrically located inside filter 82. Poppet 84 is movable between second end face 74 of annular band 68 (as shown on the right side of the break line in FIG. 4) and end wall 52 (as shown on the left side of the break line in FIG. 4). Annular band 68 further includes an annular groove 87 located in second end face 74. A seating ring 88 is fitted within annular groove 87. A biasing means such as spring 90 is provided between poppet 84 and wall 52 to urge lip 86 of poppet 84 toward seating ring 88. Thus, in its normally biased position, a seal is formed between lip 86 of poppet 84 and seating ring 88.

In the operation of the disclosed device 10, control circuit 44 causes pump 34 to draw medication from reservoir 32 and provide it to catheter 12 through tube 40 at a controlled rate. When reservoir 32 is to be refilled, a non-coring needle (shown in phantom) is injected into septum fitting 14. As the needle passes through aperture 58 it is guided to the central portion of the fitting by the conical walls of aperture 58. The needle penetrates septum 66, enters cavity 80 and contacts the bottom surface 84a of poppet 84 at the bottom of antechamber 85. The needle is forced further to move poppet 84 away from its normally biased position against annular band 68 until poppet 84 stops against end wall 52 of housing 50.

The movement of poppet 84 in response to the needle draws lip 86 away from seating ring 88 and breaks the seal therebetween. Thus antechamber 85 is in communication with reservoir 32 through annular filter 82, annular groove 54, and bore 55. Medication at atmospheric pressure is then allowed to flow through the needle and into antechamber 85 and reservoir 32 which are maintained at below-atmospheric pressure by the action of pressurant chamber 30 against diaphragm 28.

When a given volume of medication has been drawn into resevoir 32, the needle is withdrawn from antechamber 85 and septum fitting 14. As the needle is withdrawn, poppet 84 follows the movement of the needle until lip 86 engages seating ring 88 to form a secure seal therebetween. Septum fitting 14 provides an improved seal at lip 86 of poppet 84 because seating ring 88 is compressed between annular band 68 and poppet 84. Also, as the needle is withdrawn from septum 66, the internal radial forces in septum 66 developed by the compression of septum 66 between central extension 64 and central ring 76 cause septum 66 to reseal with high integrity.

While a presently preferred embodiment of the subject invention has been shown and described, the invention is not limited thereto, but can be otherwise variously embodied within the scope of the following claims.

I claim:

1. A septum fitting comprising:
   a housing having an open end and at least one passageway through the wall of said housing, said passageway being located adjacent the opposite end;
   a guide member secured in the open end of said housing and having a central aperture that extends between external and internal faces, the internal face of said guide member having a central extension that surrounds said aperture;
   a septum that is located in said housing longitudinally adjacent said guide member and contacting the internal face of said guide member; and
   an annular band that is located in said housing longitudinally adjacent said septum, said annular band having first and second end faces and an aperture that extends therebetween and that is generally aligned with the central aperture of said guide member, said annular band having a ring extension on said first end face that circumscribes said aperture and that contacts said septum, the ring extension of said annular band cooperating with the central extension of said guide member to compress the septum therebetween.

2. The septum fitting of claim 1 wherein said septum and said annular band cooperate with said housing to define a cavity, said septum fitting further comprising:
   an annular filter that is located in said cavity.

3. The septum fitting of claim 2 wherein the second face of said band includes an annular groove, said fitting further comprising:
   a poppet that is movable between the housing and the annular band;
   means for biasing said poppet against said annular band; and
   a seat that fits within the annular groove of the band and cooperates with said poppet to form a seal when said biasing means urges said poppet against said seat.

4. A septum fitting comprising:
   a generally cylindrical housing that includes a wall at one end, said housing having at least one passageway that extends between the interior and exterior surfaces of said housing, and that is located adjacent the one end;
   a guide member that is secured in the end of said housing that is oppositely disposed from the one end, said guide member having external and internal faces and a central aperture that extends between the external and internal faces, said guide member further having an extension from the internal face that circumferentially surrounds the central aperture;
   a septum that is located in said housing longitudinally adjacent said guide member and that contacts the internal face of said guide member; and
   an annular band that is located in said housing longitudinally adjacent said septum and that has first and second end faces and a central aperture that extends therebetween and that is generally aligned with the central aperture of said guide member, said annular band also having a ring extension that is located on said first end face and that circumscribes said central aperture, the ring extension and the first end face of said annular band contacting said septum and cooperating with the extension of said guide member to compress the septum therebetween.

5. The septum fitting of claim 4 further comprising:
   an annular filter that is maintained in said housing between the annular band and the end wall of said housing.

6. The septum fitting of claim 5, wherein the second face of said band includes an annular groove and wherein said fitting further comprises:
   a poppet that is movable between the end wall of the housing and the annular band;
   means for biasing said poppet against said annular band; and
   a seat that fits within the annular groove of said band and cooperates with said poppet to form a seal when said biasing means urges said poppet against said seat.

7. The septum fitting of claim 4, 5, or 6 wherein the guide member includes an external shoulder, said fitting further comprising:
   a retainer ring that is secured to the interior surface of the housing adjacent the end of the housing that is opppositely disposed from the one end, said retainer ring cooperating with the external shoulder of the guide member to maintain said guide member in said housing.

8. A septum fitting for use on an implantable medical device, said fitting comprising:
   a generally cylindrical housing that includes a wall at one end and an annular groove located in the interior surface of said housing adjacent the wall, said housing having at least one bore that extends through the wall that is in communication with the annular groove;
   a guide member secured in the end of said housing that is oppositely disposed from said wall, said guide member having external and internal faces with an aperture having a generally conical shape that extends therebetween, said guide member also having an extension from the internal face that circumferentially surrounds the aperture;

a septum that is located in said housing longitudinally adjacent said guide member and that contacts the internal face of said guide member; and an annular band that is located in said housing longitudinally adjacent said septum, said annular band having first and second end faces and a central aperture that extends therebetween and that is substantially aligned with the aperture of said guide member, said annular band also having a ring extension that is located on the first end face and that circumscribes the central aperture, the ring extension and the first end face of said annular band contacting said septum with the longitudinally separation between the ring extension of said annular band and the extension of said guide member being less than the longitudinal separation between the internal face of said guide member and the first face of said annular band such that the ring extension of said annular band cooperates with the extension of said guide member to radially compress said septum therebetween.

9. The septum fitting of claim 8 wherein the second face of said band includes an annular groove and cooperates with said septum and with said housing to form a cavity, said fitting further comprising:

an annular filter located in said cavity;

a poppet that is located in said cavity and that is concentrically arranged with respect to said annular filter, said poppet being movable between the end wall of the housing and the annular band;

means for biasing said poppet against said annular band; and a seat that fits within the annular groove of the band and cooperates with said poppet to form a seal when said biasing means urges said poppet against said seat.

* * * * *